United States Patent
Klemm et al.

(10) Patent No.: US 9,427,294 B2
(45) Date of Patent: Aug. 30, 2016

(54) METHOD FOR OPERATING AN ELECTRIC APPLIANCE AND ELECTRIC APPLIANCE

(75) Inventors: Torsten Klemm, Eschborn (DE); Ingo Vetter, Karben (DE); Uwe Jungnickel, Koenigstein (DE)

(73) Assignee: BRAUN GMBH, Kronberg (DE)

( * ) Notice: Subject to any disclaimer, the term of this patent is extended or adjusted under 35 U.S.C. 154(b) by 608 days.

(21) Appl. No.: 13/213,874

(22) Filed: Aug. 19, 2011

(65) Prior Publication Data
US 2012/0068634 A1    Mar. 22, 2012

(30) Foreign Application Priority Data

Aug. 19, 2010  (EP) .................................. 10008644
Aug. 19, 2010  (EP) .................................. 10008645
Jul. 25, 2011  (EP) .................................. 11006064

(51) Int. Cl.
| | |
|---|---|
| *G01R 27/02* | (2006.01) |
| *A61C 17/34* | (2006.01) |
| *G01R 19/00* | (2006.01) |
| *A61C 17/22* | (2006.01) |
| *H02P 25/02* | (2016.01) |

(52) U.S. Cl.
CPC ......... *A61C 17/3481* (2013.01); *A61C 17/221* (2013.01); *G01R 19/0084* (2013.01); *H02P 25/027* (2013.01)

(58) Field of Classification Search
CPC .......... G01R 9/00; G01R 9/02; G01R 17/00; G01R 17/02; G01R 17/04; G01R 17/06; G01R 17/12; G01R 19/00; G01R 19/0023; G01R 19/0038; G01R 19/0084; G01R 19/0092; G01R 19/165; G01R 19/16509; G01R 19/16566; G01R 19/16576; G01R 19/2503; G01R 19/2506; H02K 7/00; H02K 11/00; H02K 11/001; H02K 11/0015; H02K 11/0052; H02K 11/0057; H02K 11/0068; H02K 19/365; H02K 23/66; H02K 29/06; H02K 29/146; H02K 33/04; A61C 17/221; A61C 17/3481; H02P 25/027
USPC ................................. 324/606, 605, 602, 600
IPC .............. G01R 9/00, 9/02, 17/00, 17/02, 17/04, G01R 17/06, 17/12, 19/00, 19/0023, 19/0038, G01R 19/0084, 19/0092, 19/165, 19/16509, G01R 19/16566
See application file for complete search history.

(56) References Cited

U.S. PATENT DOCUMENTS

| | | |
|---|---|---|
| 6,351,089 B1 | 2/2002 | Ibuki et al. |
| 6,441,571 B1 | 8/2002 | Ibuki et al. |

(Continued)

FOREIGN PATENT DOCUMENTS

| | | |
|---|---|---|
| DE | 102004029684 A1 | 12/2005 |
| JP | 08192376 | 7/1996 |
| JP | 2001016892 | 1/2001 |

OTHER PUBLICATIONS

International Search Report and written opinion mail date Dec. 4, 2012 , 10 pages.

*Primary Examiner* — Hoai-An D Nguyen
(74) *Attorney, Agent, or Firm* — George Henry Leal; Vladimir Vitenberg

(57) ABSTRACT

An electrical appliance with a resonant motor for driving a vibratory component is provided that has a control unit for driving the resonant motor with a predetermined driving frequency and for measuring the motion-induced voltage of the resonant motor and for determining whether the measured voltage value coincides with a predetermined target voltage value or whether the measured voltage value has crossed over the predetermined target value. The control unit measures the motion-induced voltage at a predetermined time of measurement ($t_m$) within a driving cycle.

14 Claims, 2 Drawing Sheets

(56) References Cited

U.S. PATENT DOCUMENTS

| | | |
|---|---|---|
| 7,180,254 B2 | 2/2007 | Klemm et al. |
| 7,551,411 B2 * | 6/2009 | Woods et al. .................. 361/33 |
| 8,314,586 B2 | 11/2012 | Lumbantobing et al. |
| 2003/0209015 A1 * | 11/2003 | Song .................................. 62/6 |
| 2003/0233877 A1 | 12/2003 | Grez et al. |
| 2009/0243520 A1 | 10/2009 | Kashiwabara et al. |
| 2010/0109580 A1 * | 5/2010 | Lumbantobing et al. .... 318/130 |
| 2011/0197455 A1 | 8/2011 | Vetter et al. |

* cited by examiner

US 9,427,294 B2

METHOD FOR OPERATING AN ELECTRIC APPLIANCE AND ELECTRIC APPLIANCE

FIELD OF THE INVENTION

The present invention is concerned with a method for operating an electrical appliance, for example, an electric toothbrush or an electric razor, and it is further concerned with an electrical appliance comprising a control unit.

BACKGROUND OF THE INVENTION

It is known that in electrical appliances a resonant motor may be provided to drive mechanical components into vibratory motion. The resonant motor may e.g. be realized as an oscillating electric motor. Such resonant motors may be used in electric shavers or electric toothbrushes, in which a working amplitude of a driven mechanical component is created without a gearing mechanism. A mechanical component intended for vibratory motion during operation may be an armature of the resonant motor, a drive shaft, or a component coupled to the drive shaft, such as a brush head for an electric toothbrush.

To achieve good efficiency of the driving of the resonant motor, it is desirable that the driving frequency with which the resonant motor is provided, either (1) coincides with the resonance frequency of the spring-mass system determined by the resonant motor and the driven component or (2) has a certain predetermined distance to the resonance frequency.

It is known that a resonant drive of an electrical appliance can be powered by applying a supply voltage such that a drive current having a fixed frequency that is near the resonance frequency of the spring-mass system builds up. However, the resonance frequency of the relevant spring-mass system depends on several factors that can change while the electric appliance is being operated. In particular, the mechanical load on the driven mechanical component (e.g. a brush head of a toothbrush) may fluctuate, e.g. when the user changes the pressure on the bristles of a toothbrush while brushing teeth.

This may result in a certain change of the actual resonance frequency of the spring-mass system. Since in this case the efficiency and/or the performance of the small electrical appliance may diminish, it would therefore be desirable if the change in the resonance frequency can be detected to improve operation of the electric appliance.

Thus, there is a desire to provide a method and an electrical appliance in which a variation of the actual resonance frequency and/or a mechanical load on the driven vibrating component of the electrical appliance can be detected during operation in an inexpensive and easy to implement manner.

SUMMARY OF THE INVENTION

A method of operating an electrical appliance having a resonant motor for driving a vibratory component is provided, which method includes the acts of driving the resonant motor by a drive current with a predetermined driving frequency, measuring a motion-induced voltage of the resonant motor at a predetermined time of measurement within a driving cycle, and determining whether the measured voltage value coincides with a predetermined target value or whether the measured voltage value has crossed over the predetermined target value.

An electrical appliance with a resonant motor for driving a vibratory component is provided, in which the electrical appliance has a control unit for driving the resonant motor with a predetermined driving frequency. The electrical appliance further comprises a processing unit for (1) measuring at a predetermined time of measurement within a driving cycle the motion-induced voltage of the resonant motor and (2) determining whether the measured voltage value coincides with a predetermined target value or whether the measured voltage value has crossed over the predetermined target value.

BRIEF DESCRIPTION OF THE DRAWINGS

The invention is further illustrated by an exemplary embodiment and by reference to figures. In the figures

DETAILED DESCRIPTION OF THE INVENTION

Figure 1:
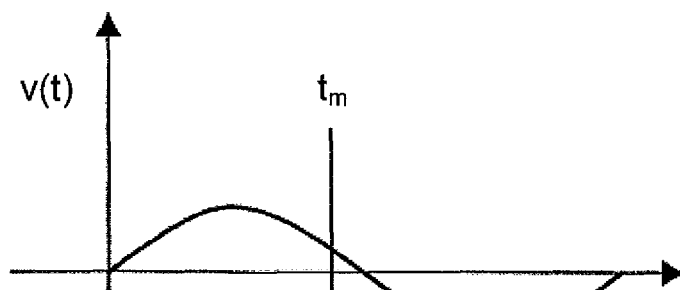
FIGS. 1-3 show the time progression of a motion-induced voltage of a resonant under different relations between the driving frequency and the (actual) resonance frequency.

A resonant motor may have a coil mounted statically with respect to a motor armature carrying at least a permanent magnet. The motor armature may be mounted such that a return force keeps the armature in a rest position or provides a return force when the armature is moved out of its rest position. The return force may be generated by a return force element such as a spring or a spring arrangement. A mechanical vibratory component may be coupled to the motor armature. When a periodically changing supply voltage is provided with a driving frequency at the coil, an alternating current flow through the motor coil is generated and the electromagnetic field of the coil interacts with the armature carrying the permanent magnet such that the armature is brought into an oscillatory or vibratory motion, which motion also drives the mechanical vibratory component coupled to the motor armature. The resonant motor represents a spring-mass system that has a resonance frequency determined by the relevant spring constant and the relevant mass. The closer the driving frequency is to the resonance frequency the more efficient is the driving, i.e. the highest amplitude of the driven periodic movement of the motor armature is achieved when the driving frequency coincides with the resonance frequency.

A difference between the driving frequency and the actual resonance frequency of a spring-mass system having a resonant motor leads to certain phase shift between the periodic driving force and the driven periodic movement of the motor armature. The driven periodic movement determines the motion-induced voltage at the coil of the resonant motor induced by the moving permanent magnet. Hence, any change in the driving frequency (e.g. by controllably changing the driving frequency) or in the actual resonance frequency (e.g. by applying a mechanical load at a driven mechanical component) results in a change in this phase shift. Thus, a certain relationship between driving frequency and actual resonance frequency can be determined when the motion-induced voltage reaches a predetermined target value at a certain time instant within a driving cycle. Hence, it can be determined whether the driving frequency coincides with the (actual) resonance frequency or has a certain distance from the (actual) resonance frequency. Additionally, it may be determined if a certain mechanical load is applied to the driven mechanical component as this is reflected by a certain value of the motion-induced voltage at a certain time of measurement within the driving cycle.

If the motion-induced voltage reaches (or crosses over) a predetermined value at the time of measurement while the driving frequency is fixed, this may be an indication that a predetermined mechanical load is being applied at the driven mechanical component. If a predetermined target value is measured during a constant load state (e.g. during a no-load state), this indicates that the driving frequency and the resonance frequency have a predetermined distance (which distance may be zero or may have a non-zero value). As an example, if the predetermined target value were 2 V, the motion-induced voltage "crosses over" when a first measured motion-induced voltage is above the predetermined target value and a subsequent measured motion-induced voltage is below the predetermined target value. As another example, the motion-induced voltage "crosses over" when a first measured motion-induced voltage is below the predetermined target value and a subsequent measured motion-induced voltage is above the predetermined target value.

In case that a predetermined target voltage value is measured, this may be indicated by an acoustical, optical or tactile signal. The audible and/or visual and/or tactile signal can alert the user of the electrical appliance that the applied mechanical load is too high. If the signal indicates a change in load, and thus a deviation from optimal performance, the user can change the handling of electric appliance. Thus, the user can intuitively optimize handling of the electric appliance.

The time of measurement can be selected such that it is near a zero crossing of the motion-induced voltage when the resonant motor is mechanically unloaded. A wave form, e.g. the motion-induced voltage, can have portions which are above the abscissa (horizontal or x-axis) and below the abscissa. The zero crossing is where the waveform crosses or intersects the abscissa.

The time of measurement may be selected so that a zero crossing of the motion-induced voltage is reached at the time of measurement when a predetermined mechanical load is applied at the driven mechanical component (e.g. a brush head). A zero crossing of the motion-induced voltage may be more easily detectable than a certain absolute target voltage value. A zero-crossing can e.g. be detected (within a certain uncertainty limit) by detecting a sign change in the motion-induced voltage between successive measurements.

In some embodiments, the motion-induced voltage can be tapped at the coil of the resonant motor and a comparator unit may be applied to compare the measured voltage value with a predetermined target voltage value.

The reference voltage value may be zero Volt (0 V).

In some embodiments, the comparator unit may be arranged to provide a binary output signal depending on the comparison result, wherein the output signal provided may be fed into a processing unit.

In some embodiments, the control unit may be arranged to change the driving frequency between successive measurements of the motion-induced voltage. In case that the measurement time is chosen such that a zero-crossing of the motion-induced voltage occurs when the driving frequency and the resonance frequency have a predetermined distance, it is thus enabled that the control unit automatically can detect its optimal driving frequency, independent from effects like tolerances or aging of motor parts.

The method of controlling an electrical appliance with a resonant motor and a respective electric appliance are described in more detail using the example of an electric toothbrush, which should not be interpreted as limiting.

An electric toothbrush brush may have a hand piece with a resonant motor having a drive shaft at which a mechanical vibratory component in the form of a brush head can be attached. The resonant motor can set the brush head into oscillation. The spring-mass system determined by the resonant motor and the mechanical vibratory component (here: brush head) has a specific resonance frequency. The actual resonance frequency changes, inter alia, when a mechanical load is applied. During use, mechanical load can, e.g., be exerted by the pressure of the brush head on the tooth surface.

To achieve high efficiency, the resonant motor may be powered by supplying an alternating supply voltage with a predetermined driving frequency to the resonant motor, where the driving frequency may be chosen to have a predetermined distance to the resonance frequency of the spring-mass system. The driven periodic movement has the same frequency as the driving frequency.

In some embodiments, a change in the actual resonance frequency of the spring-mass system (e.g. due to an applied mechanical load) is used to detect whether the mechanical load coincides with a predetermined load value. To detect the change in the actual resonance frequency, the motion-induced voltage which is induced by the moving magnets in the coil of the resonant motor is measured and analyzed at a predetermined time of measurement. In order to measure the motion-induced voltage directly at the resonant motor, a current flow through the motor coil may be switched off after a driving phase within a driving cycle. When no current flow through the coil, the voltage that can be tapped from the resonant motor is the motion-induced voltage can be tapped, e.g. measured, as the self-induced voltage and the voltage at the ohmic resistance of the resonant motor dissipate with the cessation of the current flow. U.S. Pat. No. 7,180,254, the content of which shall be enclosed in the present disclosure by reference, describes the different components of the voltage across the coil of a resonant motor.

FIG. 1 shows the velocity versus time v(t) of a moving motor armature carrying permanent magnets of the resonant motor without mechanical load applied on the vibratory mechanism. The motion-induced voltage u(t) induced in the static coil of the resonant motor due to the changing magnetic field provided by the moving permanent magnets is proportional to the velocity v(t) of the moving armature. The frequency of the motion-induced voltage u(t) thereby corresponds to the driving frequency. The driving frequency itself is here assumed to be above the resonance frequency of the resonant motor. For example, the resonance frequency of the resonant motor may be in a range of between about 30 Hz to about 500 Hz and the driving frequency may have an offset to the resonance frequency in a range of between about 1 Hz to about 50 Hz.

Figure 3:
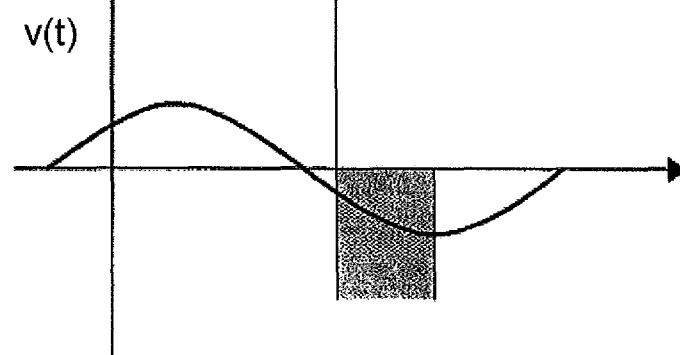

FIG. 3 likewise shows the velocity versus time v(t) of the moving armature for a case where the driving frequency is below the resonance frequency of the resonant motor. This situation may occur when a load is applied at the resonant motor which shifts the actual resonance frequency such that the actual resonance frequency has increased to a value above the driving frequency, with the driving frequency being kept constant. Such a situation can also occur when the driving frequency is changed while the resonant motor is kept in an unloaded state.

In some embodiments, the time of measurement $t_m$ at which the motion-induced voltage is measured and analyzed, may be selected such that it is close to a zero crossing of the motion-induced voltage. In FIG. 1, the time of measurement $t_m$ occurs prior to the zero crossing; in FIG. 3 it occurs after the zero crossing, so that, according to FIG. 1, the measured motion-induced voltage is greater than zero at time $t_m$ and according to FIG. 3, the measured motion-induced voltage is less than zero at time $t_m$.

If the resonant motor (driving the mechanical component, e.g. a brush head of an electric toothbrush) is mechanically loaded during operation, its resonance frequency changes, e.g. because the mechanical load affects at least one of the effective spring constant and/or the effective mass/mass inertia of the spring-mass system determined by the resonant motor and the driven component. A change in the resonance frequency leads to a change in the phase shift between the periodic driving force and the driven periodic movement of the motor armature such that at a fixed time of measurement $t_m$ within a driving cycle the measured value of the motion-induced voltage changes from a previously measured value of the motion-induced voltage. As FIG. 3 shows a case where the resonance frequency has shifted from being below to being above the driving frequency, the zero crossing of the velocity versus time v(t) also crossed over the time of measurement $t_m$. Additionally, because the motion-induced voltage u(t) is proportional to the velocity v(t) it is expected that u(t) may similarly cross over.

Figure 2:
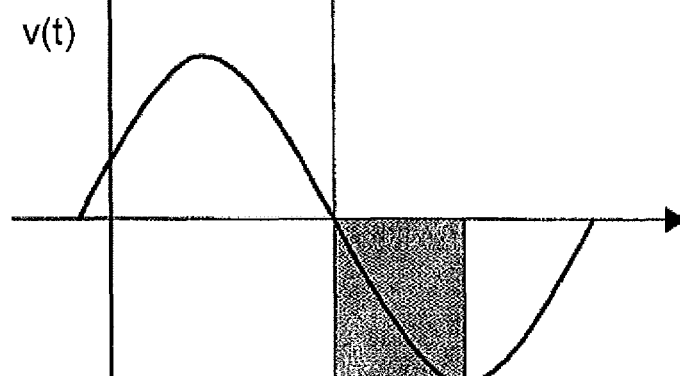

FIG. 2 shows the velocity versus time v(t) of the armature of the resonant motor at a situation where either the mechanical load is such that the phase shift has moved the zero crossing of the velocity versus time to the time of measurement $t_m$ or where the driving frequency was changed such that the phase shift has moved the zero crossing of the velocity versus time to the time of measurement $t_m$.

The time of measurement can now be selected such that the zero crossing of the motion-induced voltage lies at the time of measurement under the condition that a predetermined mechanical load is reached or that the driving frequency and the resonance frequency have a predetermined relation (i.e. the distance between driving frequency and the resonance frequency has a predetermined value, e.g. +5 Hz or −8 Hz etc.). In case that a load has shifted the resonance frequency, the system may be designed such that the actual resonance frequency and the driving frequency coincide at a desired load value. Then the system works with higher efficiency, which is reflected by the higher velocity of the moving armature as indicated by the velocity versus time v(t) in FIG. 2.

Instead of determining whether the motion-induced voltage has a zero crossing at the time of measurement, it may also be chosen to determine whether the motion-induced voltage has any other value besides zero Volts. A zero crossing (0 V) may tend to be detectable with a more simple electronic circuitry. In some embodiments, it is detected that a load above the predetermined load is applied when a sign change in the motion-induced voltage is detected between successive measurements.

If, at the time of measurement $t_m$, a zero crossing of the motion-induced voltage is detected, or if the motion-induced voltage reaches a predetermined voltage value at the time of measurement $t_m$, this may be indicated to a user. This can be done, for example via an indicator device for outputting a visible, audible, and/or tactile signal.

Thus, a mechanical load on the resonant motor can be determined directly from the motion-induced voltage. An additional sensor for detecting a mechanical load or for measuring the actual peak amplitude of e.g. the motor armature is not required.

The method according to the invention is not limited to use in electric toothbrushes. Rather, it may also be used in other electrical devices with resonant motors, such as electric shavers and household appliances.

Figure 4:
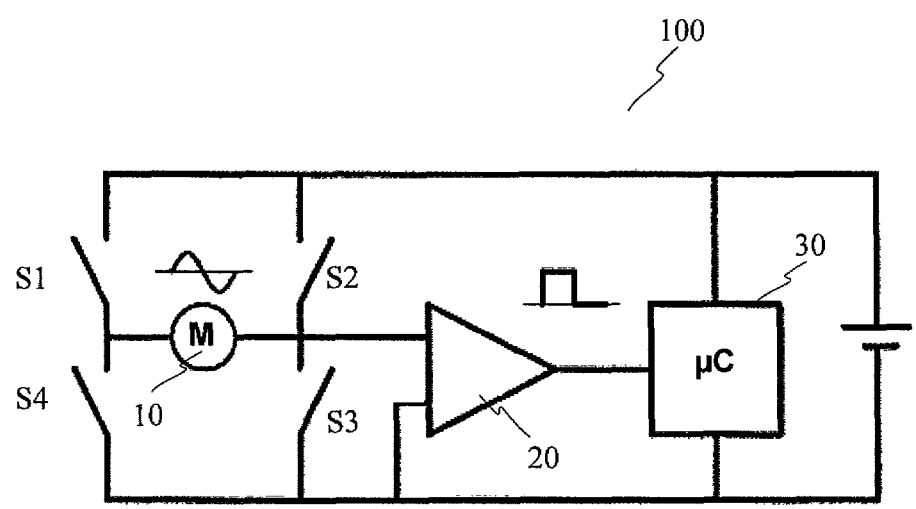
FIG. 4 is a block diagram of a circuit layout for controlling a resonant motor.

FIG. 4 shows a block diagram of a possible circuit configuration for driving a resonant motor 10 and for detecting a mechanical load on a vibratory mechanism in a small electrical device by analyzing the motion-induced voltage.

For driving the electric motor 10 a full bridge circuit with four switches, i.e. S1, S2, S3, and S4, can be provided, in the shunt arm of which the electric motor 10 is arranged. The full bridge circuit is connected to a control unit 30. The four switches of the full bridge circuit, which can be designed as transistors, for example, are controlled by the control unit 30. The switches, e.g. S1, S2, S3, and S4, may be controlled in a conventional manner such that the current flowing through the electric motor periodically changes direction. If switches S1 and S3 are closed while switches S2 and S4 are open, current flows through switches S1 and S3 through the electric motor. If switches S2 and S4 are closed while switches S1 and S3 are open, a current flows through the electric motor in the opposite direction, through switches S2 and S4.

A current flow through the resonant motor 10 may be switched off by opening all four switches. The control unit 30 may be arranged to switch off the current flow through the motor for a certain time period in each driving cycle. When the current flow has ceased, the motion-induced voltage can be directly tapped from the resonant motor. The motion-induced voltage may thus be measured in successive driving cycles to determine whether the predetermined voltage value is reached. In some embodiments, the switches S1 to S4 may be realized as MOSFETs.

The voltage tapped from the resonant motor 10 may be fed to a comparator unit 20. The voltage provided at the comparator unit 20 can then be measured at the predetermined time of measurement within a driving cycle. Analysis of the motion-induced voltage can be carried out using the processes described above with reference to FIG. 1 through FIG. 3. In order to determine whether the motion-induced voltage has reached a predetermined voltage value (e.g. 0 V), the comparator unit 20 may be provided with a reference voltage (e.g. 0 V) which corresponds to the predetermined voltage value.

As a result of the comparison, the comparator unit 20 provides a signal at its output (with high or low level) which is supplied to the control unit 30. If the measured motion-induced voltage and the predetermined voltage value match, for example, if a zero crossing of the motion-induced voltage is present at the time of measurement, a high level can be applied at the output of the comparator unit 20. In some embodiments, a high level output is provided by the comparator unit 20 when a positive voltage is measured and a low-level signal is provided when a negative voltage is measured or vice versa.

The control unit 30 may be arranged to analyze the output from the comparator unit 20 and, depending on the analysis, perform a predetermined action. A predetermined action can be, for example, creating a visual or audible or tactile signal if the comparator unit 20 indicates that the zero crossing is reached or that the zero crossing was crossed.

In some embodiments, the control unit 30 may be arranged to change the driving frequency by a preselected amount between successive measurements until the motion-induced voltage has reached the predetermined voltage value. By such a procedure, the driving frequency can be automatically set at or close to the resonance frequency such that tolerances between different resonant motors and/or aging effects changing the resonance frequency can be coped with and the resonant motor can always be driven with high efficiency.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of operating a hand-held electrical appliance selected from the group consisting of an electrical toothbrush and an electrical razor, the appliance comprising a resonant motor for driving a vibratory component, the method comprising the steps of:
    driving the resonant motor with a predetermined driving frequency and constant duty cycle;
    measuring a motion-induced voltage of the resonant motor at a predetermined time of measurement ($t_m$) within a driving cycle;
    determining a phase shift by measuring whether the motion-induced voltage value coincides with or crosses over a predetermined target voltage; and
    generating a signal when the measured voltage value has reached or exceeded the target value in response to an increase in mechanical load that causes a phase shift, the signal being selected from the group consisting of an acoustic signal, an optical signal, and a tactile signal.

2. The method according to claim 1, wherein the time of measurement ($t_m$) is selected such that the measured voltage value in a mechanically unloaded state of the resonant motor is close to zero Volt.

3. The method according to one of claim 1, wherein the time of measurement is selected such that the measured voltage value essentially coincides with the predetermined target voltage value at a predetermined load value applied at the resonant motor.

4. The method according to one of claim 1, further comprising the act of repeatedly changing the driving frequency by a preselected amount prior to repeating the acts of driving, measuring and determining until the predetermined target voltage value is achieved or crossed over.

5. The method according to claim 1, wherein the measured voltage value is applied at a comparator unit, which comparator unit is supplied with a predetermined reference voltage for comparison with the measured voltage value.

6. The method according to claim 5, wherein the reference voltage is 0 Volt.

7. The method according to claim 5, wherein the comparator unit provides a binary single-digit output signal as a function of the comparison, which output signal is fed to a processing device.

8. An electrical appliance with a resonant motor for driving a vibratory component, comprising a control unit for driving the resonant motor with a predetermined driving frequency and constant duty cycle, and for measuring at a predetermined time of measurement ($t_m$) within a driving cycle the motion-induced voltage of the resonant motor and for determining a phase shift by measuring whether the voltage-induced voltage coincides with or crosses over a predetermined target voltage, wherein the electrical appliance comprises an indicator device for outputting a signal when the measured voltage value has reached or exceeded the target value, the signal being selected from the group consisting of an acoustic signal, an optical signal, and a tactile signal, and wherein the motion-induced voltage is caused by an increase of a mechanical load on the resonant motor, the electrical appliance being selected from the group consisting of an electrical toothbrush and an electrical razor.

9. The electric appliance according to claim 8, wherein the control unit is arranged for changing the driving frequency between successive measurements of the motion-induced voltage when the measured voltage value does not coincide with the predetermined target voltage value.

10. The electric appliance according to claim 8, further comprising a comparator unit arranged for comparing the measured voltage value with a predetermined reference voltage, which optionally is 0 Volt.

11. The electrical appliance according to claim 8, wherein the time of measurement is selected such that, in the case of a mechanically unloaded resonant motor, the time of measurement is located near a zero crossing of the motion-induced voltage and/or wherein the time of measurement is selected such that, with a mechanical load on the resonant motor at the time of measurement, a zero crossing of the motion-induced voltage occurs at a predetermined load applied at the resonant motor.

12. The electrical appliance according to claim 11, wherein the comparator unit is arranged to provide a binary output signal as a function of the comparison, which can be fed to the control unit.

13. The electric appliance according to claim 8, wherein the control unit is arranged for performing the measurement of the motion-induced voltage while no current flows through the resonant motor.

14. The electric appliance according to claim 13, wherein the control unit is arranged to switch off the current flow through the resonant motor prior to the time of measurement.

* * * * *